(12) United States Patent
Gaudillat

(10) Patent No.: US 8,026,196 B2
(45) Date of Patent: Sep. 27, 2011

(54) DELAYED-EFFECT AGRONOMIC TREATMENT AGENT, IN PARTICULAR FOR SEED GERMINATION AND PLANT DEVELOPMENT

(75) Inventor: Michel Gaudillat, Buc (FR)

(73) Assignee: Clause (FR)

( * ) Notice: Subject to any disclaimer, the term of this patent is extended or adjusted under 35 U.S.C. 154(b) by 137 days.

(21) Appl. No.: 12/282,136

(22) PCT Filed: Mar. 8, 2006

(86) PCT No.: PCT/FR2006/000517
§ 371 (c)(1),
(2), (4) Date: Feb. 24, 2009

(87) PCT Pub. No.: WO2007/101917
PCT Pub. Date: Sep. 13, 2007

(65) Prior Publication Data
US 2009/0199314 A1    Aug. 6, 2009

(51) Int. Cl.
*A01N 25/28* (2006.01)
*A01N 25/00* (2006.01)
*A01N 25/12* (2006.01)
*A01H 5/00* (2006.01)

(52) U.S. Cl. ........ 504/359; 504/117; 504/367; 514/772; 800/298

(58) Field of Classification Search .................. None
See application file for complete search history.

(56) References Cited

U.S. PATENT DOCUMENTS 5,221,535 A    6/1993    Domb

FOREIGN PATENT DOCUMENTS

| EP | 0 018 119 | 10/1980 |
|---|---|---|
| WO | 83/00799 | 3/1983 |
| WO | 91/01803 | 2/1991 |
| WO | 99/63817 | 12/1999 |
| WO | 00/48465 | 8/2000 |
| WO | 02/057862 | 7/2002 |
| WO | 03/061383 | 7/2003 |
| WO | 2004/034791 | 4/2004 |

OTHER PUBLICATIONS

Henton et al. Polylactic Acid Technology Feb. 11, 2005 chapter 16. http://www.jimluntllc.com/pdfs/polylactic_acid_technology.pdf.*
Mario Casolaro Thermodynamics of multiple stimuli responsive polyelectrolytes with complexing ability towards the copper(II) ion. Reactive Polymers vol. 23, Issues 2-3 Oct. 1994. Abstract.*
International Search Report; PCT/FR2006/000517; Jun. 5, 2007.

* cited by examiner

*Primary Examiner* — Annette Para
(74) *Attorney, Agent, or Firm* — Cantor Colburn LLP

(57) ABSTRACT

Agent for the agronomic treatment of a living plant supported by a moist substrate, for example a soil, wherein said agent is in the solid and divided state, and comprises solid particles containing at least one active entity for the agronomic treatment, characterized in that each particle comprises:—a nucleus consisting of a grain of a solid material which is inert with respect to the substrate, comprising an inner developed surface area which is greater than its apparent surface area and, as a result, suitable for adsorption and/or absorption, —the active entity for agronomic treatment, absorbed into the grain and/or adsorbed at the surface of said grain, —a membrane encapsulating the nucleus comprising the active entity, consisting of at least one hydrophilic polymer which is permeable to the outside with respect to the active entity, when it is in direct or indirect contact with the moist substrate.

31 Claims, 1 Drawing Sheet alkyd resin (addition of glycerol + o-phthalic acid + fatty acid)

DELAYED-EFFECT AGRONOMIC TREATMENT AGENT, IN PARTICULAR FOR SEED GERMINATION AND PLANT DEVELOPMENT

TECHNICAL FIELD OF THE INVENTION

The present invention relates generally to the agronomic treatment of plants, for different purposes, whether it is a matter of stimulating the germination of the seeds, promoting the growth of the plants, or protecting them against various pathogens or parasites.

The invention more specifically relates to non-aerial agronomic treatment, i.e. treatment using a humid substrate, for example using a soil, in which the plant of interest lives or is cultivated. For example, the present invention will be explained and described with reference to the treatment of seeds, for example of species especially of vegetable garden, floral and large-scale farming varieties, or alternatively of tree and shrub seeds.

BRIEF DESCRIPTION OF RELATED ART

For the purposes of treating plants, in particular seeds, for example using a humid feedsoil, it is known practice to obtain, produce and provide the treating agent in solid and divided form, i.e. comprising solid particles comprising the individual or combined active species for the treatment, whether it is, for example, a plant nutrient, enhancing microorganisms, or products for disinfecting the environment of the seeds and plants.

Two main embodiments of such a treating agent are proposed or described in practice.

According to a first mode, each particle comprises a grain constituted by a mineral or synthetic solid material, which adsorbs and/or absorbs the active species; cf. for example, bacteria on a peat substrate.

This mode does not make it possible, on the one hand, to control the release of the active species into the humid substrate, and, on the other hand, to protect said species for as long as possible against the moisture existing in or provided to said substrate, for example during any temporary hydration prior to the action phase of the active species.

According to a second mode, each particle consists of a capsule, microcapsule or nanocapsule, comprising a membrane, for example obtained with a polymer of natural origin, encapsulating the individual or combined active species; cf. for example, microencapsulated essential oils.

This mode does not show sufficient mechanical strength allowing the capsules to withstand either an attrition-generating post-treatment, for example during coating or film-treating in a humid phase, or direct deposition in the substrate, for example as a mixture with seeds in a seeder.

For the purposes of obtaining an agronomic treatment, in solid and divided form, which is directly or indirectly suitable for incorporation on contact with and into a substrate, for example a soil, which is by nature humid or liable to be hydrated, one subject of the present invention is a system for conditioning or forming the active species of the agronomic treatment, simultaneously allowing, on the one hand, good mechanical strength, in particular with respect to crushing or to pressure, and also good resistance to temporary hydration during the preparation of the final product to be used, and, on the other hand, a controlled or controllable release over time of the active species, precisely by means of the humidity or water available or provided to the substrate.

BRIEF SUMMARY OF THE INVENTION

According to the present invention, each particle comprises:
- a core constituted by a grain of a solid material that is inert, i.e. with respect to the substrate, comprising an inner developed surface that is greater than its apparent surface, which is in particular porous (inter- and/or intra-porosity), and accordingly suitable for adsorption and/or absorption of the active species alone, or supported by a liquid phase, for example,
- the active species of the agronomic treatment, as defined previously, absorbed into the grain and/or adsorbed onto the surface of the grain or of its constituent particles,
- a membrane encapsulating the core, comprising the active species, which is itself absorbed onto and/or adsorbed into said core as stated previously, this membrane being constituted by at least one hydrophilic polymer, which is outwardly permeable with respect to the active species, when it is in direct or indirect contact with the humid substrate.

Two embodiments should then be considered.

According to a first embodiment of the invention, the treating agent defined previously is used directly in the substrate and, for example, provided in a soil, together and as a mixture with seeds.

According to this first embodiment, the system defined previously makes it possible, via a suitable choice of the constituent hydrophilic polymer(s) of the membrane, which is (are) more or less soluble and/or hydratable in aqueous phase, and of their thickness, to modify the outward permeability of the membrane with respect to the active species, in particular under the effect of the humidity, and, on the whole, to release the active species, locally (in situ) into the substrate, according to any suitable temporal planning, for example immediately, or within a few days, or within a few weeks.

If it is desired to provide the plant with different active species, which are mutually incompatible or which neutralize each other, the system according to the present invention makes it possible to obtain treating agents that are respectively different, with releases respectively staggered over time, but nevertheless provided together in the soil, for example in the root area of the plant.

The conditioning or forming system according to the present invention constitutes an effective and efficient alternative to the extemporaneous application of the active species for the agronomic treatment.

This system makes it possible in particular to avoid any loss of active species, not only during the storage of the treating agent, by oxidation, evaporation, etc., but also during the application, by temporary rehumidification, etc.

The conditioning system according to the invention also makes it possible to obtain a treating agent, in solid and divided form, and in a dry state, which is compatible with the current techniques for deposition in a soil, on plants or on seeds, for example in terms of size of the particles, flow, wettability and durability.

According to a second embodiment of the invention, which is particularly preferred, each particle of the treating agent defined previously also comprises another membrane, encapsulating the core comprising the active species, which is itself already encapsulated by the membrane defined previously, i.e. constituted by at least one hydrophilic polymer, this said other membrane being constituted by at least one hydrophobic polymer, which can be broken down on contact with the humid substrate.

By virtue of the other membrane, it is possible to protect the treating agents against any temporary hydration, which would otherwise be liable to cause the liberation or release of the active species. This protection is in particular important when the treating agent is coated or film-treated, for example around seeds, with a disintegrable material, of glue type, provided in a humid phase, and then dried.

The treating agent according to the invention then withstands, i.e. practically preserves all its properties for release of the active species, once in the humid substrate.

The conditioning system according to the present invention also makes it possible to preserve the activity of the active species (cf. viability of a microorganism), during the storage of the treating agent, up to the time when it is liberated or released, but also during the coating or film-treating of said agent.

Such a temporary protection also has an advantage in the substrate, by allowing release of the active species, not at the time of placing of the seed in the soil, for example, but once said seed has been placed in a hydrated medium, or even in hydrated soil.

In summary, the conditioning system according to the invention allows the active species to act, when it is needed, and where it is needed, in the region of the seed during germination, and then in the area of development of the root network of the plant, or of its crown, and only after application.

In particular, by virtue of the invention, the treating agent may be applied to and stored in operative form on the seeds themselves, relative to their storage conditions before sowing.

Via a suitable choice of the hydrophilic and hydrophobic polymers, respectively, on the one hand, and of the inert solid material, on the other hand, the conditioning system according to the invention is degradable and without risk to the environment.

The term "inert" means the property by which the material under consideration is without risk to the environment and/or the cultivated plant.

The term "disintegrable" means the property by which the material under consideration disintegrates, and thus loses all cohesion, by dissolution, passing into suspension, swelling, chemical or enzymatic hydrolysis, chemical or biological degradation, biodegradation, bioassimilation, etc.

The present invention presents the following implementation variants, which may be considered alone or in combination.

The mean diameter of the solid particles of the agronomic treating agent according to the invention is between 5 and 500 µm, preferentially between 5 and 50 µm and, for example, about 13 µm, depending on the selected application process.

The hydrophilic polymer, which is the main or sole constituent of the membrane of the solid particles, is by nature film-forming and/or emulsifying. It is chosen, for example, from the group constituted by polyvinylpyrrolidone (PVP), polyvinyl alcohols (PVA), waxes, alginates, chitosan, modified or unmodified polyosides, including polysaccharides, modified or unmodified starches, celluloses, dextrins, maltodextrins, gum arabic, guar gum, acacia gum, gelatins and proteins (soybean, whey).

The solid material of the particles of the treating agent according to the invention is inert in the sense that its introduction into the substrate, for example a soil, presents virtually no adverse effects, including toxicity, not only with respect to said substrate, but also with respect to the plant during cultivation. It is preferentially a mineral material chosen from the group constituted by zeolites, montmorillonites, calcium carbonate, silicas, diatomaceous earths, including infusorial earth or kieselguhr, and pumices.

By way of example, the mineral material is a modified diatomaceous earth, obtained by hydrothermic reaction between a siliceous diatom, hydrated lime, and water.

However, in certain cases, the inert solid material of the particles is a nonmineral material, for example an organic material, chosen from the group constituted by synthetic organic polymers, including macroporous polystyrenes, polyacrylates, microporous styrene matrices, and heat-shrinkable polymers (for example polyacrylamides).

According to the present invention, the term "solid material" means any material that has size stability under the conditions of use of the agronomic treating agent, in particular with respect to temperature and relative humidity.

Preferentially, the grain of the inert solid material, constituting the core of the particles of the treating agent according to the invention, has the form of a microsphere. This form may be obtained in particular by a spheronization step, according to the production process described below.

This grain preferentially has a macroporous structure, this porosity equally being inter-porosity or intra-porosity, for instance in the case of the diatomaceous earths illustrated hereinbelow. By way of example, the specific surface area (BET) relative to the area of the porous inert solid material, is at least equal to 50, preferentially between 50 and 200, and, for example, equal to about 140 m$^2$/g.

According to the applications or uses, which depend on the nature of the active species used, the weight ratio of said active species relative to the grains of inert solid material is at least equal to $10^{-9}$, preferentially between $10^{-6}$ and 1, and, for example, equal to about 0.40.

The hydrophilic polymer may be chosen to become insoluble in water at and above a temperature at least equal to 30° C., for example at and above a temperature of 45° C., for example the hydroxypropylcellulose sold under the name KLUCEL®, or at and above 70° C., for example polyacrylamides (HDC). It may also be an alginate placed in contact with calcium ions.

Such a property is advantageous when, as described hereinbelow, another membrane of hydrophobic nature is placed on the particle, using an aqueous phase at relatively high temperature, for example by coalescence; in such a case, the hydrophilic polymer membrane is thus preserved.

According to the present invention, all kinds of active species may thus be conditioned or formed, depending on the agronomic treatment used.

They may first be products that stimulate the germination of seeds, i.e. molecules that are physiologically active on germination.

The active species may be a product that promotes the growth of plants, for example hormones, or that increases their resistance to environmental stresses, for example defense stimulators, or that stabilizes the pH of the substrate and its immediate surroundings, or alternatively a nutrient.

It may also be a product for protecting against agents that are unfavorable toward the growth of young plants, including herein viruses and pathogenic microorganisms, for example a fungicidal, bactericidal, hematicidal, insecticidal or herbicidal product, which acts by contact, ingestion or gaseous diffusion; it is, for example, any suitable essential oil, for example extract of thyme. All these products reinforce the resistance reactions of the plant, and/or disinfect or regulate the environment of said plant.

The active species may be a live biological material, for example a nonpathogenic microorganism, for example at least one fungus, or a bacterium, or a virus, if necessary with a medium ensuring its viability; and this microorganism, for example of the pseudomonas, bacillus, trichoderma, clonostachys, fusarium, rhizoctonia, etc. type stimulates the growth of the plant, or protects it against the pathogens defined previously.

When the agronomic treating agent according to the invention comprises another membrane, i.e. two membranes, the first encapsulating the core comprising the active species, and the second coating the first membrane, itself constituted by a disintegrable hydrophobic polymer, the following implementation variants should be considered:
- the hydrophobic polymer is chosen from the group constituted by synthetic polymers, including poly(3-hydroxyoctanoate) (THO), polyhydroxyalkanoate (THA), polylactic acids of different molecular weights (PLA), poly(3-hydroxybutyrate-co-3-hydrovalerate) (PHVA), poly-ϵ-caprolactone (PCL), butyl styreneacrylate, polyethylene terephthalate (PET), glycol-lactic copolymers, alkyd resins, modified starches, alginates, chitosans and polysaccharides;
- preferentially, the hydrophobic polymer is a polylactic acid with a molar mass of between 5000 and 100 000 or an alkyd resin.

The invention also relates to a process for obtaining an agronomic agent having, for example, the structure and/or the morphology defined previously.

According to this process:
a) inert material, in solid and divided form, is provided,
b) the active species selected for the agronomic treatment, in liquid phase, is provided,
c) a hydrophilic polymer in aqueous phase is provided,
d) the solid inert material in divided form, comprising an internal developed surface area that is greater than its apparent surface area, for example a porous material, is impregnated with the active species in liquid phase, to obtain an intermediate material, which is still solid and in divided form, comprising the active species,
e) this intermediate material is coated with the hydrophilic polymer in aqueous phase, to obtain globules,
f) the water is removed from the globules, to obtain a powder that may constitute the desired agronomic treating agent.

Preferentially, during step (f), the water is removed especially in a fluidized airbed or by nebulization-drying.

By way of example, steps (e) and (f) are performed simultaneously, by fluidizing the intermediate material, and by spraying thereon the hydrophilic polymer in aqueous phase, the whole in a stream of air, for example a stream of hot air, to coalesce said polymer. The drying conditions, especially the rate of drying and the air temperature, are adapted to obtain a satisfactory membrane.

During step (d) defined previously, the impregnation conditions are predetermined to charge the inert material, in solid and divided form, with a mass amount of the active species in liquid phase, of between 20% and 200%, preferentially between 30% and 50%, and, for example, equal to about 43% of the initial mass of the active species in liquid phase.

Alternatively, preferentially, the hydrophilic polymer of the aqueous phase represents at least 1% and preferentially 5% to 10% by weight of said aqueous phase, to obtain a viscosity that is suitable for impregnating the intermediate material.

By way of example, when the hydrophilic polymer is HPC, this polymer is dissolved in water at a rate of from 1% to 10% (m/m) of the aqueous phase, and, after impregnation according to step (e) at the surface of the intermediate material with the aqueous solution, followed by drying according to step (f), the dry polymer represents 5% to 50% (m/m) of said intermediate material.

When it is an agronomic treating agent, the grains of which comprise a hydrophilic and hydrophobic, respectively, double membrane, the powder obtained at the end of the process defined previously may be taken for further steps according to which:
- this powder is thus provided,
- and a disintegrable hydrophobic polymer in aqueous phase is provided, and:
g) the powder is coated with the hydrophobic polymer in aqueous phase, to obtain globules,
h) the water is removed from the globules, to obtain the desired agronomic treating agent.

Preferentially:
- the hydrophobic polymer in aqueous phase is a latex or a microsuspension or nanosuspension of said polymer in water,
- steps (g) and (h) defined previously are performed simultaneously, by fluidizing the powder, and spraying thereon the hydrophobic polymer in aqueous phase, the whole in a stream of air.

For example, the suspension comprises 10% (m/m) of the hydrophobic polymer relative to the aqueous phase, and after drying the same hydrophobic polymer, in dry form, represents from 10% to 50% (m/m) of the powder subjected to steps (g) and (h).

If this is required, the process described previously may comprise a step of spheronization of the treating agent, after any step of water removal.

The agronomic treating agent according to the invention may be used by placing it directly on a substrate, for example a soil, or it may be combined with plant material for reproduction or multiplication of a plant species, especially a plant variety, in divided form, for example seeds, which material is then placed in the feed substrate. In the latter case, each discrete component of the abovementioned plant material, for example seeds, is coated or film-treated with a matrix of a water-permeable and optionally disintegrable material, incorporating the treating agent according to the invention, distributed in said matrix.

Such material consists, for example, of a seed of a species, especially of a vegetable garden, floral or large-scale farming variety, or alternatively seeds of trees or shrubs.

As stated previously, when a coating or film-treating operation is performed with a disintegrable material, in humid form or in an aqueous phase, the second membrane, or other membrane, of the particles of the agronomic treating agent makes it possible to withstand the temporary hydration thus performed, until complete drying of the coated or film-treated plant material, and does so while preserving the structure and activity of the agronomic treating agent.

In summary, the present invention relates to any agronomic treatment, according to which plant material for reproduction or multiplication of a species, especially a plant variety, for example seeds, is provided in a humid or hydrated substrate, for example a soil, according to which a treating agent as defined previously is placed in the same substrate, such that the active species of the agronomic treatment is released or liberated in the immediate vicinity of the seed or in the area of rooting or of the crown of the plant species under consideration, undergoing development or growth.

Two variants of such a process may be considered:
- according to a first variant, for example extemporaneously, the agronomic treating agent is mixed with the plant material for reproduction or multiplication, which is itself in solid and divided form, and the mixture thus obtained, still in solid and divided form, is placed in the humid substrate,
- according to a second variant, before placing it in the humid substrate, the agronomic treating agent is or becomes combined, integrally, with the plant material for reproduction or multiplication, in solid and divided form, for example by coating or film-treating as described previously.

DETAILED DESCRIPTION OF THE INVENTION

Figure 1:
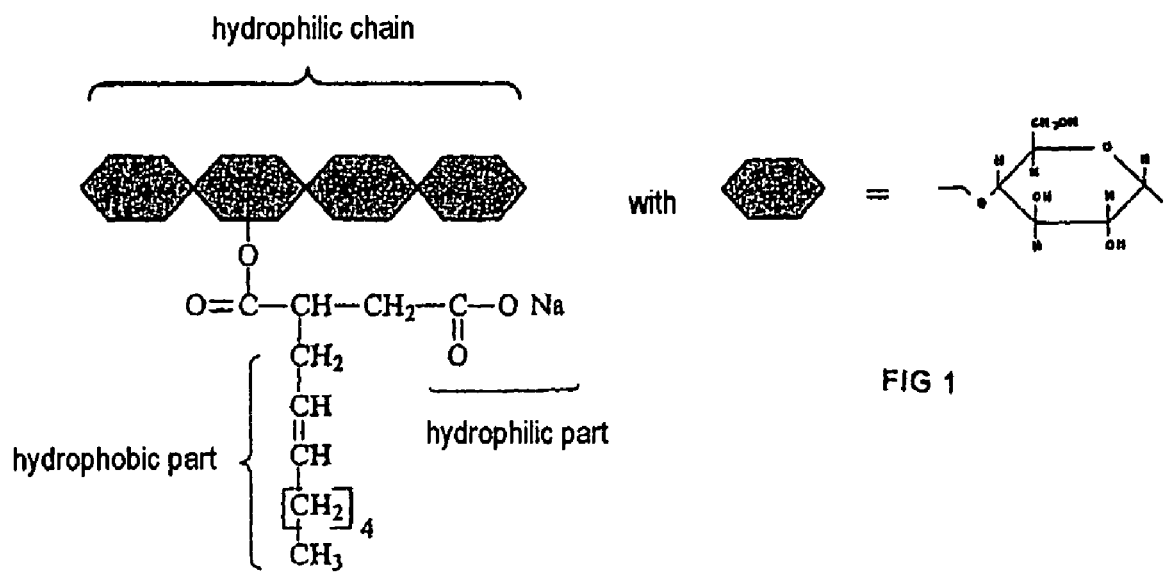
FIG. 1 shows the chemical formula of CLEARGUM®.

The examples that follow illustrate the present invention.

Example 1

Production of an Intermediate Material, in Solid and Divided Form, from a Porous Mineral Material in Solid and Divided Form, and from an Active Species in Liquid Phase According to this example, the active species for the agronomic treatment consists of an essential oil having, in a known manner, a disinfecting and protective action against pathogens in a soil. This essential oil is, for example, essential oil of thyme, manufactured and sold by the company Flore de Saintonge, under the name Hethyt 600R. This essential oil will be referred to hereinbelow as HE.

According to this example, the porous mineral material in solid and divided form is a modified diatomaceous earth, i.e. by reaction between a siliceous diatom, hydrated lime, and water, for example the product solid by the company World Minerals under the name CALFLO C®.

The grains of this material are irregular and angular, and have a morphology offering intra-porosity and inter-porosity, having overall a specific surface area of 140 $m^2\ g^{-1}$ (BET point) relative to air. The diameter of the grains is from about 5 to 50 µm, with a mean size of 13 µm.

The following experimental protocol is performed. Before impregnation, the CALFLO C is washed with distilled water, in order to remove the impurities, and placed in an oven under vacuum at a temperature of 80° C. for one day.

The following experimental protocol is then performed:
1. The CALFLO C, referred to hereinbelow as TdD, is screened;
2. The TdD is impregnated, as described hereinbelow, so as to obtain various mass contents of impregnation with HE (mass of HE relative to the total mass TdD+HE), respectively, of 20%, 33%, 43% and 50% m/m; to do this it suffices to vary the duration of the impregnation described hereinbelow.
3. Next, the liberation/release kinetics of the HE, by gaseous diffusion, are measured by monitoring the weight loss over time.

As regards the impregnation, the HE and TdD are introduced into a 100 ml pill bottle, with agate beads in order for the HE to be uniformly distributed in the TdD, and for the interstitial sites of the TdD to be accessible. The pill bottle is agitated for 20 minutes in a roll mixer. After this operation, the TdD has become uniformly impregnated with HE. Scanning microscopy images (SEM), before and after mixing, show that the blending in the mixer does not affect the size of the TdD grains.

The amount of HE retained in and impregnating the TdD is measured according to the following operating protocol:
  extraction of the HE with dichloromethane ($CH_2Cl_2$);
  assay of the HE in the dichloromethane in the ultraviolet range, at 273 nm.

To give the intermediate material the form of a dry powder, a degree of impregnation (mass of HE relative to the total mass of TdD and HE) of 43% is chosen.

The release kinetics in open air are monitored by simple weighing, or thermogravimetric analysis (TGA).

Two successive release steps are observed, by desorption:
  a first step of rapid desorption, which may correspond to the loss of the HE multilayers, covering the fractal surface of the TdD;
  and a second step of slower desorption, which may correspond to the loss of the HE retained in the inter- and intra-grain porosities of the TdD.

Virtually all the HE retained in the TdD may thus be released relatively quickly.

Example 2

Encapsulation of the Intermediate Material Obtained According to Example 1 with a Hydrophilic Polymer, to Obtain a Powder Intermediate material, referred to hereinbelow as Mi, as obtained according to Example 1, and consequently in the form of micrograins, is thus provided.

It is chosen to coat these grains with a hydrophilic polymer in aqueous phase. The hydrophilic polymer selected is degradable.

In the laboratory, the abovementioned intermediate material is encapsulated according to the dry emulsion protocol below:
1. an aqueous solution of the hydrophilic polymer is provided;
2. the Mi is dispersed in this aqueous solution to obtain a dispersion;
3. the aqueous dispersion is spread onto glass plates, and the water is evaporated off in a controlled manner, to precipitate by coalescence or coacervation the hydrophilic polymer around the grains of the Mi, and to obtain a powder.

Figure 2:
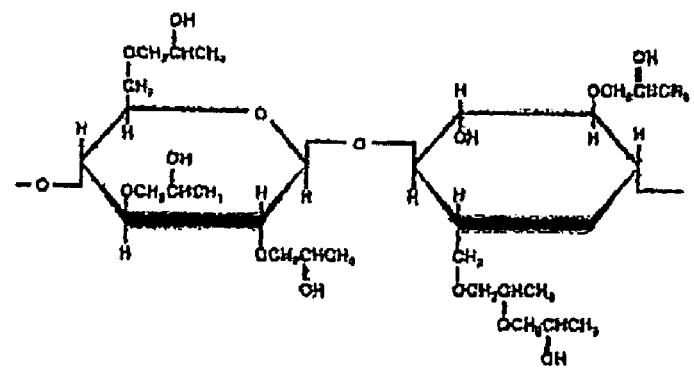
FIG. 2 shows the chemical formula of KLUCEL®.

Two hydrophilic polymers were selected and tested, namely:
  a modified starch, for example the product sold by the company Roquette under the name CLEARGUM®, corresponding to the chemical formula given in FIG. 1;
  a hydroxypropylcellulose, for example the product sold by the company Aqualon under the name KLUCEL®, corresponding to the chemical formula shown in FIG. 2.

As regards KLUCEL®, it should be noted that it is insoluble in water from 45° C., which makes it possible, as shown hereinbelow in Example 4, to subsequently coat the powder obtained according to the present example with a hydrophobic polymer (polylactic acid or alkyd resin) in aqueous phase and under warm conditions, without any risk of dissolving or of causing swelling of the membrane (or first membrane) of the hydrophilic polymer.

In the KLUCEL range, various grades were used, known as J and M, which differ from each other by their molecular weight, i.e., respectively, 140 000 and 850 000.

The following experimental protocol is used:
1. an Mi obtained according to Example 1, containing 43% (m/m) of HE, is used as starting material;
2. an aqueous solution of a hydrophilic polymer chosen as indicated previously, at 1% or 2% by weight of said polymer relative to the weight of water, is provided;
3. using a deflocculating paddle rotating at 1000 rpm, at room temperature, the aqueous solution from (2) is stirred, and the Mi is added to obtain an aqueous dispersion of the Mi, stirred for 1 minute, the Mi representing in all the tests reported hereinbelow 20% by weight of the aqueous dispersion, i.e. of the total weight Mi plus aqueous polymer solution; the dispersion step is performed while keeping the mass of the Mi constant, and while varying the mass of the hydrophilic polymer encapsulating the grains of the Mi, and while varying the mass of the hydrophilic polymer encapsulating the grains of the Mi; it is chosen, however, to apply a minimum amount of hydrophilic polymer around the grains of the Mi.
4. according to the same dry emulsion protocol as that described in Example 1, the dispersion obtained is deposited and spread out on various glass plates, in thin layers,
5. the plates are then placed in the open air, under a fume cupboard, for 1 to 2 hours; the surface humidity decreases rapidly; when the degree of humidity reaches 7% to 23%, the encapsulation membrane obtained is semipermeable, i.e. it allows the diffusion of water, while at the same time retaining or slowing down the diffusion of the compounds of the HE, 6. once the capsules are dry, they are recovered and separated, if necessary, by very light mortar grinding, to obtain a powder, 7. using the powder thus obtained, the HE impregnation yield is calculated, by measuring the amount of HE retained in the powder, as indicated previously; and the kinetics of diffusion of the HE in open air are observed, by monitoring the weight loss of the powder, with 1 g of said powder placed in a crucible under a ventilated fume cupboard.

The results of the encapsulation tests are given in Table I.

From this table, the following observations may be made:

The yields obtained are satisfactory and greater than 66%.

For the same molar mass, when the amount of polymer increases and when the viscosity increases, the encapsulation yields are improved.

For the same amount of hydrophilic polymer deposited and at the same concentration of polymer in the solution (and approximately same drying time), the yields obtained with hydroxypropylcellulose of high molar mass (850 000 g.mol$^{-1}$) are higher than those resulting from the encapsulations with hydroxypropylcellulose of low molar mass (140 000 g.mol$^{-1}$). The higher viscosity of this solution explains these observations.

TABLE I

| | | Initial mixtures | | Finished products (powder) | | | | |
|---|---|---|---|---|---|---|---|---|
| | | Aqueous solution | Mass of polymer | | | | | |
| Tests | Hydrophilic polymer | \|polymer\|$_{water}$ g/100 g H$_2$O | relative to (m (Mi) | % TdD | % HE | % polym | Drying time | Yield (HE) |
| T1 | HPC 80 000 g.mol$^{-1}$ | 1% | 5% | 54.42 | 40.82 | 4.76 | 1 h 30-2 h | 67% |
| T2 | HPC 80 000 g.mol$^{-1}$ | 2% | 10% | 51.95 | 38.96 | 9.09 | 1 h 30-2 h | 74% |
| T4 | modified starch | 1% | 5% | 54.42 | 40.82 | 4.76 | 1 h 30-2 h | 55% |
| T5 | modified starch | 2% | 10% | 51.95 | 38.96 | 9.09 | 1 h 30-2 h | 56% |

HPC (80 000 g/mol$^{-1}$) = KLUCEL ® E
CLEARGUM ® = modified starch
Mi = TdD + HE The yields of HE encapsulated in the powder obtained are correct. The yield increases when the concentration of the hydrophilic polymer in the water increases. When the encapsulation is performed under warm conditions (65° C.), the yield decreases.

As regards the release, the following observations are made:
- a thicker membrane wall slows down the diffusion of the HE;
- the oblique asymptote is, however, reached more slowly for the grains of Mi encapsulated with HPC than for the modified starch (for example CLEARGUM). The asymptote moreover becomes all the more horizontal, and for longer retention times, the higher the molar mass of HPC and the larger the amount deposited around the Mi grains.

Thus, by varying the KLUCEL® range, it can be determined whether the viscosity, the mass or the amount of hydrophilic polymer influences the release of HE.

During the encapsulation, the molar mass of the HPC is thus varied.

The procedure is the same as previously. The encapsulation yield is calculated as previously.

The results are collated in Table II below:

On the whole, irrespective of the molar mass of the HPC, the diffusion is slowed down when the amount of hydrophilic polymer increases.

As regards the kinetics, all the release curves have the same shape: a relatively rapid rise corresponding either to poorly coated grains or to a more or less fissured membrane wall ("burst" effects are observed in most of the diffusions), followed by a rise to a horizontal asymptote that is proportionately slower the thicker the membrane.

Example 3

Encapsulation of the Powder Obtained According to Example 2 with a Hydrophobic Polymer, to Obtain an Agronomic Treating Agent in Solid and Divided Form In general, according to this example, a powder as obtained according to Example 2 is provided and, using a hydrophobic polymer that has a good water-barrier effect, and a relatively rapid rate of degradation in the soil, an aqueous dispersion of said polymer is formed. Next, the powder is coated with the

TABLE II

| | | Aqueous solution | | Finished products (powder) | | | | |
|---|---|---|---|---|---|---|---|---|
| Tests | Mw g · mol$^{-1}$ | \|polymer\| (g/100 g H$_2$O) | polymer (g/100 g Mi) | % TdD | % HE | % polym | Drying time (air) | Yield (HE) |
| T1 | 140 000 | 1% | 5% | 54.42 | 40.82 | 4.76 | 1 h 40 | 66% |
| T2 | 140 000 | 2% | 10% | 51.95 | 38.96 | 9.09 | 1 h 40 | 68% |
| T3 | 850 000 | 1% | 5% | 54.42 | 40.82 | 4.76 | 1 h 10 | 74% |
| T4 | 850 000 | 2% | 10% | 51.95 | 38.96 | 9.09 | 1 h 30 | 80% | hydrophobic polymer, to obtain globules, and the water is removed from these globules to obtain the desired treating agent.

The hydrophobic polymer used is a poly(lactic acid) or PLA, in the form of nanoparticles dispersed in water, PLA being particularly advantageous on account of its film-forming nature, and of its possible degradation by controlled hydrolysis according to its molar mass.

Figure 3:
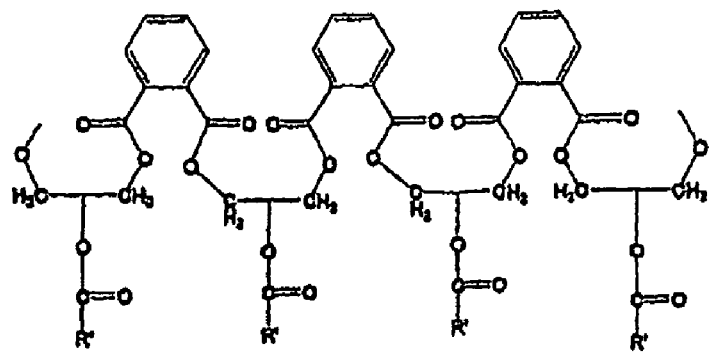
FIG. 3 shows the chemical formula of an alkyd resin.

The hydrophobic polymer used is also a film-forming alkyd resin, dispersed in water in the form of nanoparticles, and generally corresponding to the chemical formula according to FIG. 3; for example, the resin Uradil AZ 554-Z50 manufactured and sold by the company DSM, which requires for its crosslinking a drying agent, namely Nuodex Combi AQ, which is also sold by the company DSM.

The film formation of this resin is obtained first by coalescence, and then by drying power.

Two series of tests, performed with different PLAs, were performed, respectively, under laboratory conditions, by dry emulsion on a plate, and under industrial conditions, by application in a fluidized airbed but according to the dry emulsion technique.

Various redispersible aqueous suspensions of PLA as colloidal nanoparticles were obtained and were tested, preliminarily, to coat fertilizer granules, in order to determine the optimum application and film-forming (formation of a membrane) operating conditions.

Having established these operating conditions, two different PLAs were tested, one of low molar mass, i.e. 7000, with a Tg of 45° C., and the other of higher molar mass, i.e. 35 000, with a Tg of 55° C.

The following operating protocol is then followed.
1. A powder (microparticles) as obtained according to Example 2 is provided. Tow types of powder were tested:
    the first whose microparticles each contain a TdD+HE core (HE representing by weight 43% of the total weight of TdD+HE), and an HPC membrane with a molecular weight of 80 000, the membrane representing 5% or 50% (m/m) of the core (TdD+HE),
    the second whose microparticles each contain a TdD+HE core (HE representing by weight 43% of the total weight of TdD+HE), and an HPC membrane with a molecular weight of 850 000, the membrane representing 5% or 50% (m/m) of the core (TdD+HE).
2. a PLA latex in an aqueous base is provided, the PLA representing 15% (m/v) of the aqueous phase; the two PLAs of different molecular weight identified above were tested,
3. the powder is dispersed in the latex, with a deflocculating paddle rotating at 800 rpm, for one minute, at 45°, to obtain an aqueous dispersion,
4. according to the dry emulsion technique, the aqueous dispersion is spread onto glass plates, which are then dried in an oven at 58° C. for 30 to 45 minutes, and the particles thus obtained are then recovered, optionally after separation in a mortar,
5. on these particles, three determinations are performed:
    the yield of HE encapsulated by the double membrane is calculated, according to the method described previously,
    the diffusion kinetics in open air are determined, by monitoring the weight loss of the particles,
    the diffusion kinetics are determined by mixing and incorporating the particles in sand, and by determining the residual amount of HE in the particles, according to the same method.

The test results obtained, by dry emulsion in the laboratory, are collated in Table III below:

TABLE III

| Tests | Mw(HPC) g·mol$^{-1}$ | HPC (g/100 g$_{Mi}$) | Mw(PLA) g/mol$^{-1}$ | PLA (g/100 g$_{powder}$) | Finished products | | | | Yield (HE 2nd encaps.) | Yield (overall HE) |
|---|---|---|---|---|---|---|---|---|---|---|
| | | | | | % TdD | % HE | % HPC | % PLA | | |
| T1  | 80 000  | 5%  | 7000   | 10% | 49.47 | 37.11 | 4.33  | 9.09  | —   | —   |
| T2  | 850 000 | 5%  | 7000   | 10% | 49.47 | 37.11 | 4.33  | 9.09  | 41% | 35% |
| T3  | 80 000  | 50% | 7000   | 10% | 34.63 | 25.97 | 30.30 | 9.09  | 57% | 42% |
| T4  | 80 000  | 5%  | 7000   | 50% | 36.28 | 27.21 | 3.17  | 33.33 | 54% | 36% |
| T5  | 850 000 | 5%  | 7000   | 50% | 36.28 | 27.21 | 3.17  | 33.33 | 45% | 38% |
| T6  | 80 000  | 50% | 7000   | 50% | 25.40 | 19.05 | 22.22 | 33.33 | 58% | 43% |
| T7  | 80 000  | 5%  | 35 000 | 10% | 49.47 | 37.11 | 4.33  | 9.09  | 64% | 43% |
| T8  | 850 000 | 5%  | 35 000 | 10% | 49.47 | 37.11 | 4.33  | 9.09  | 39% | 33% |
| T9  | 80 000  | 50% | 35 000 | 10% | 34.63 | 25.97 | 30.30 | 9.09  | 73% | 54% |
| T10 | 80 000  | 5%  | 35 000 | 50% | 36.28 | 27.21 | 3.17  | 33.33 | 63% | 42% |
| T11 | 850 000 | 5%  | 35 000 | 50% | 36.28 | 27.21 | 3.17  | 33.33 | 55% | 47% |
| T12 | 80 000  | 50% | 35 000 | 50% | 25.40 | 19.05 | 22.22 | 33.33 | 60% | 44% |

Mi = TdD + HE
Powder = TdD + HE + HPC

The term "yield of the second encapsulation" means the amount of HE present in the particles, after encapsulation with the hydrophobic polymer, relative to the amount of HE initially present in the powder.

The term "overall yield" means the amount of HE remaining in the particles, after encapsulation with the hydrophobic polymer, relative to the initial amount of HE used to impregnate the TdD.

The following observations are then made:
    the yield for the second encapsulation, by dry emulsion, ranges from 41% to 73%; during this step, the HPC protects the HE against diffusion,
    the overall yield does not change with the mass of PLA deposited on the powder,
    the diffusion in open air is appreciably retarded by increasing the amount of PLA applied during the second encapsulation,
    the diffusion in sand shows that a release delayed by 30 days may be achieved, for example for an application of the type such as seeds in a humid substrate.

As regards the tests of industrial type, these were performed under industrial dry emulsion conditions, with a fluidized bed used with a "Mini-Glatt" machine, manufactured and sold by the company Glatt.

With this machine, the powder obtained according to Example 2 is fluidized, to obtain a fluidized bed, and the hydrophobic polymer as an aqueous dispersion is sprayed onto the powder thus fluidized, the whole in a stream of hot air, by means of which, as in the laboratory, the powder is coated with the hydrophobic polymer, to obtain droplets in gaseous suspension, and the water is removed from these droplets to obtain the desired treating agent.

For the tests reported hereinbelow, the abovementioned machine is used in the following manner:
- the process air is set and controlled at a temperature of 80° C. and at a pressure of 0.8 bar,
- 20 g of the powder are introduced into the product tank,
- the hydrophobic polymer dispersion comprises 10% dry extract, and is sprayed at a liquid flow rate of 2-3 ml/minute and at a spraying air pressure of 0.8 bar,
- the internal temperature in the spraying cone is maintained at 50° C.

The results of tests of second encapsulation of dry emulsion type in a fluidized bed are collated in Table IV below:

TABLE IV

| Tests | Mw(HPC) g·mol$^{-1}$ | HPC (g/100 g$_{Mi}$) | Mw(PLA) g/mol$^{-1}$ | PLA (g/100 g$_{powder}$) | Finished products | | | | Yield (HE 2nd encaps.) | Yield (overall HE) |
|---|---|---|---|---|---|---|---|---|---|---|
| | | | | | % TdD | % HE | % HPC | % PLA | | |
| T1 | 80 000 | 5% | 7000 | 10% | 49.47 | 37.11 | 4.33 | 9.09 | 96% | 64% |
| T2 | 850 000 | 5% | 7000 | 10% | 49.47 | 37.11 | 4.33 | 9.09 | 59% | 50% |
| T3 | 80 000 | 50% | 7000 | 10% | 34.63 | 25.97 | 30.30 | 9.09 | 73% | 54% |
| T4 | 80 000 | 5% | 7000 | 50% | 36.28 | 27.21 | 3.17 | 33.33 | 75% | 50% |
| T5 | 850 000 | 5% | 7000 | 50% | 36.28 | 27.21 | 3.17 | 33.33 | 67% | 57% |
| T6 | 80 000 | 50% | 7000 | 50% | 25.40 | 19.05 | 22.22 | 33.33 | 74% | 55% |
| T10 | 80 000 | 5% | 35 000 | 10% | 49.47 | 37.11 | 4.33 | 9.09 | 84% | 56% |
| T11 | 850 000 | 5% | 35 000 | 10% | 49.47 | 37.11 | 4.33 | 9.09 | 64% | 54% |
| T12 | 80 000 | 50% | 35 000 | 10% | 34.63 | 25.97 | 30.30 | 9.09 | 81% | 60% |
| T13 | 80 000 | 5% | 35 000 | 50% | 36.28 | 27.21 | 3.17 | 33.33 | 88% | 59% |
| T14 | 850 000 | 5% | 35 000 | 50% | 36.28 | 27.21 | 3.17 | 33.33 | 40% | 34% |
| T15 | 80 000 | 50% | 35 000 | 50% | 25.40 | 19.05 | 22.22 | 33.33 | 70% | 47% |

Mi = TdD + HE
Powder = TdD + HE + HPC

The following observations may be made:
- better yields are obtained in a fluidized bed than under laboratory conditions,
- the diffusion kinetics in open air show that the release in open air is better controlled by a second encapsulation performed in a fluidized airbed.

Still under industrial fluidized bed conditions, with the same machine as that defined previously, with the alkyd resin identified previously, the following results were obtained, and are collated in Table V.

TABLE V

| Tests | Mw(HPC) g·mol$^{-1}$ | HPC (g/100 g$_{Mi}$) | Alkyd resin | AR (g/100 g$_{powder}$) | Finished products | | | | Yield (HE 2nd encaps.) | Yield (overall HE) |
|---|---|---|---|---|---|---|---|---|---|---|
| | | | | | % TdD | % HE | % HPC | % AR | | |
| T1 | 80 000 | 5% | AZ | 10% | 49.47 | 37.11 | 4.33 | 9.09 | 96% | 67% |
| T2 | 850 000 | 5% | AZ | 10% | 49.47 | 37.11 | 4.33 | 9.09 | 60% | 51% |
| T3 | 80 000 | 50% | AZ | 10% | 34.63 | 25.97 | 30.30 | 9.09 | 99% | 75% |
| T4 | 80 000 | 5% | AZ | 50% | 36.28 | 27.21 | 3.17 | 33.33 | 87% | 58% |
| T5 | 850 000 | 5% | AZ | 50% | 36.28 | 27.21 | 3.17 | 33.33 | 36% | 31% |
| T6 | 80 000 | 50% | AZ | 50% | 25.40 | 19.05 | 22.22 | 33.33 | 58% | 43% |

Mi = TdD + HE
Powder = TdD + HE + HPC
AZ: Uradil AZ 554-Z50 + drying agents
AR = alkyd resin From this table and from the diffusion kinetics in open air, stoppage of the diffusion in open air is observed, after a first degassing.

Further, from the diffusions in sand, it is observed that, after deposition in a humid substrate, the diffusion is initiated only after a delay of fifteen days.

Example 4

Tests of Encapsulation of Biological Agents

As regards an agronomic treatment active species, of the microorganism type, tests of microencapsulation of bacteria were performed with *Pseudomonas fluorescens*, according to the experimental protocol described hereinbelow, of dry emulsion type in a laboratory. In such a case, the agronomic objective is to obtain rapid release of this bacterium after sowing.

A suspension of bacteria in standard medium, chosen to promote survival during dehydration and bacteriological aftergrowth of the microorganisms, with centrifugation, is prepared, until a suspension of $5.86 \times 10^{10}$ CFU/ml is obtained.

A TdD is impregnated to the maximum with the suspension obtained previously: 87 ml of suspension per 1.7 g of TdD, maintained for 15 minutes with stirring.

The excess liquid is removed to obtain a solid, divided intermediate material. This intermediate material is microencapsulated by adding 2 g of KLUCEL® (molecular weight 140 000) in the form of a solution diluted to 10% in water per 1 g of "inoculated" intermediate material, i.e. 100 g of solution per 100 g of powder. The whole is stirred for 15 minutes.

The particles or globules thus obtained are dried in open air for 2 hours 30 minutes at 25° C. and then for 5 minutes at 35° C.

There is no second encapsulation.

The bacterial population during storage in encapsulated form, at 6° C., is monitored. To this end, for each test, 0.22 g of powder is dispersed in 20 cm³ of water:
initial suspension 5.86×10¹⁰ CFU/ml
30 minutes after encapsulation=4.6×10⁸ CFU/ml
24 hours after encapsulation=1.9×10⁸ CFU/ml
10 days after encapsulation=1.35×10⁸ CFU/ml
29 days after encapsulation=8.3×10⁶ CFU/ml Since the conservation of *Pseudomonas* is particularly difficult, it is seen that the system according to the invention makes it possible to conserve and distribute this microorganism in dehydrated form (35% to 60% relative humidity at equilibrium).

The invention claimed is:

1. An agronomic treating agent for a live plant supported by a humid substrate wherein said agronomic treating agent, being in solid and divided form, comprises solid particles, wherein each particle comprises:
a core comprising a grain of a solid material that is inert with respect to the substrate, comprising an inner developed surface that is greater than its apparent surface;
an active species of an agronomic treatment, absorbed into said grain and/or adsorbed onto a surface of said grain;
a membrane encapsulating said core, comprising at least one hydrophilic polymer, which is outwardly permeable, with respect to the active species, when it is in direct or indirect contact with said humid substrate; and
an outer membrane encapsulating said core comprising at least one hydrophobic polymer, which is disintegrable on contact with the substrate.

2. The agent as claimed in claim 1, wherein a mean diameter of said solid particles is between 5 and 500 μm.

3. The agent as claimed in claim 1, wherein the hydrophilic polymer is chosen from the group consisting of polyvinylpyrrolidone (PVP), polyvinyl alcohols (PVA), alginates, chitosan, modified polyosides, unmodified polyosides, modified starches, unmodified starches, celluloses, dextrins, maltodextrins, gum arabic, guar gum, acacia gum, gelatins, soybean proteins, and whey proteins.

4. The agent as claimed in claim 1, wherein said solid material is a mineral material chosen from the group consisting of zeolites, montmorillonites, calcium carbonate, silicas, diatomaceous earths, and pumices.

5. The agent as claimed in claim 4, wherein the mineral material comprises a modified diatomaceous earth, obtained by a hydrothermal reaction between a siliceous diatom, hydrated lime, and water.

6. The agent as claimed in claim 1, wherein said solid material is a nonmineral chosen from the group consisting of macroporous polystyrenes, polyacrylates, microporous styrene matrices, and heat-shrinkable polymers.

7. The agent as claimed in claim 1, wherein said grain has a form of a microsphere.

8. The agent as claimed in claim 1, wherein said grain has a macroporous structure.

9. The agent as claimed in claim 1, wherein a specific surface area (BET), relative to the area of said solid material, is at least equal to 50 m²/g.

10. The agent as claimed in claim 1, wherein a weight ratio of the agronomic treatment active species, relative to said solid material, is at least equal to $10^{-9}$.

11. The agent as claimed in claim 1, wherein the hydrophilic polymer is insoluble in water at and above a temperature of at least 30° C.

12. The agent as claimed in claim 1, wherein the active species for the agronomic treatment comprises a product that stimulates germination of seeds.

13. The agent as claimed in claim 1, wherein the active species for the agronomic treatment comprises a product that promotes plant growth.

14. The agent as claimed in claim 1, wherein the active species for the agronomic treatment comprises a product for protecting against agents that are unfavorable for growth of young plants.

15. The agent as claimed in claim 1, wherein the active species for the agronomic treatment comprises a microorganism, which stimulates growth of a plant, or which protects said plant against pathogens.

16. The agent as claimed in claim 1, wherein the hydrophobic polymer is chosen from the group consisting of synthetic polymers, poly(3-hydroxyoctanoate) (THO), polyhydroxyalkanoate (THA), polylactic acids (PLA), poly(3-hydroxy-butyrate-co-3-hydrovalerate) (PHVA), poly-ε-caprolactone (PCL), butyl styreneacrylate, polyethylene terephthalate (PET), glycol-lactic copolymers, alkyd resins, modified starches, alginates, chitosans, and polysaccharides.

17. The agent as claimed in claim 1, wherein the hydrophobic polymer comprises a polylactic acid with a molar mass of between 5,000 and 100,000, or an alkyd resin.

18. A process for obtaining the agronomic treating agent of claim 1 comprising:
a) providing an inert material in solid and divided form, wherein said inert material comprises an internal developed surface area is greater than its apparent surface area;
b) providing an active species in liquid phase selected for an agronomic treatment;
c) providing a hydrophilic polymer in an aqueous phase;
d) providing a hydrophobic polymer, which is disintegrable in an aqueous phase;
e) impregnating said inert material with the active species in liquid phase, to obtain an intermediate material, which is solid and in divided form, whereby said intermediate material comprises an active species;
f) coating said intermediate material with said hydrophilic polymer in an aqueous phase, whereby obtaining intermediate globules;
g) removing water from said intermediate globules, whereby obtaining an intermediate powder constituting an intermediate treating agent;
h) coating said intermediate powder with said hydrophobic polymer in an aqueous phase, to obtain globules;
i) removing water from said globules, whereby obtaining said agronomic treating agent.

19. The process as claimed in claim 18, wherein water is removed according to "dry emulsion" techniques.

20. The process as claimed in claim 18, wherein impregnation conditions are predetermined to charge the inert material with a mass amount of the active species in liquid phase, between 20% and 200%, of the initial mass of the active species in liquid phase.

21. The process as claimed in claim 18, wherein steps (e) and (f) are performed simultaneously, by fluidizing the intermediate material, and by spraying thereon the hydrophilic polymer in aqueous phase, the whole in a stream of air.

22. The process as claimed in claim 18, wherein said hydrophilic polymer comprises at least 1%, by weight, of said aqueous phase.

23. The process as claimed in claim 22, wherein said hydrophobic polymer in an aqueous phase comprises a latex, a microsuspension, or a nanosuspension in water.

24. The process as claimed in claim 22, wherein steps (g) and (h) are performed simultaneously, by fluidizing the intermediate powder, and spraying thereon the hydrophobic polymer in aqueous phase, the whole in a stream of air.

25. The process as claimed in claim 18, further comprising a step of spheronization of either treating agents.

26. An agronomic treating agent that may be obtained via a process as claimed in claim 18.

27. A plant material, in divided form, for reproduction or multiplication of a plant species comprising discrete components, wherein each discrete component is coated or film-treated with a matrix of a disintegrable material incorporating a treating agent as claimed in claim 1.

28. The material as claimed in claim 27, wherein said plant material comprises a seed of a plant species.

29. An agronomic treatment process, comprising:
providing a plant material, for reproduction or multiplication of a species, in a humid substrate; and
providing an agronomic treating agent, as claimed in claim 1, in said humid substrate, whereby an active species for the agronomic treatment process is released into a rooting area or a crown area of a developing plant species.

30. The process as claimed in claim 29, further comprising mixing said agronomic treating agent, in solid and divided form, with said plant material; and
placing a mixture thus obtained in said humid substrate.

31. The process as claimed in claim 29, further comprising integrally combining said agronomic treating agent with said plant material, before placing it in said humid substrate.

* * * * *